United States Patent
Renganath et al.

(10) Patent No.: US 9,101,486 B2
(45) Date of Patent: Aug. 11, 2015

(54) SELF-DISTRACTING CAGE

(75) Inventors: Naren Renganath, Burlington, MA (US); Steve Connolly, Sharon, MA (US); Michael Alan Fisher, Lawrenceville, GA (US); Glen Arthur Presbrey, Pascoag, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 195 days.

(21) Appl. No.: 13/561,271

(22) Filed: Jul. 30, 2012

(65) Prior Publication Data

US 2012/0316652 A1 Dec. 13, 2012

Related U.S. Application Data

(62) Division of application No. 11/750,113, filed on May 17, 2007, now Pat. No. 8,273,124.

(51) Int. Cl.
*A61F 2/44* (2006.01)
*A61F 2/46* (2006.01)
(Continued)

(52) U.S. Cl.
CPC .............. *A61F 2/4455* (2013.01); *A61F 2/441* (2013.01); *A61F 2/4611* (2013.01); *A61F 2/30742* (2013.01); *A61F 2/4465* (2013.01); *A61F 2002/3055* (2013.01); *A61F 2002/30433* (2013.01); *A61F 2002/30538* (2013.01); *A61F 2002/30583* (2013.01);
(Continued)

(58) Field of Classification Search
CPC ........... A61F 2/44; A61F 2/441; A61F 2/442; A61F 2/4425; A61F 2002/443; A61F 2/4455; A61F 2002/4475

USPC ............................................ 623/17.11–17.16
See application file for complete search history.

(56) References Cited

U.S. PATENT DOCUMENTS 4,932,975 A 6/1990 Main et al.
5,236,460 A 8/1993 Barber
(Continued)

FOREIGN PATENT DOCUMENTS

WO 2004047691 6/2004
WO 2008144175 A1 11/2008

OTHER PUBLICATIONS

Written Opinion of the International Searching Authority for PCT/US08/61858, Sep. 17, 2008 (4 pages).
(Continued)

*Primary Examiner* — Jerry Cumberledge
(74) *Attorney, Agent, or Firm* — Nutter McClennen & Fish LLP

(57) ABSTRACT

Various spinal implants and methods for stabilizing the spine are provided. In one exemplary embodiment, a spinal implant is provided having an expandable container with an interior volume that is selectively expandable between a compressed condition and an expanded condition. The expandable container is coupled to a superior endplate member having a bone-contacting surface and an engagement surface effective to mate with a superior surface of the expandable container, and an inferior endplate member having a bone-contacting surface and an engagement surface effective to mate with an inferior surface of the expandable container. In addition, at least one inlet port is formed in the expandable container and is effective to communicate a fluid to at least one cavity disposed within the interior volume of the expandable container.

20 Claims, 13 Drawing Sheets

(51) Int. Cl.
*A61F 2/30* (2006.01)
*A61F 2/48* (2006.01)

(52) U.S. Cl.
CPC ............... *A61F 2002/30586* (2013.01); *A61F 2002/30601* (2013.01); *A61F 2002/4693* (2013.01); *A61F 2002/485* (2013.01); *A61F 2210/0085* (2013.01); *A61F 2220/0041* (2013.01); *A61F 2250/0006* (2013.01)

(56) References Cited

U.S. PATENT DOCUMENTS

| | | | | |
|---|---|---|---|---|
| 5,749,916 | A * | 5/1998 | Richelsoph | 623/17.16 |
| 5,893,889 | A | 4/1999 | Harrington | |
| 6,102,950 | A * | 8/2000 | Vaccaro | 623/17.16 |
| 6,190,413 | B1 | 2/2001 | Sutcliffe | |
| 6,290,724 | B1 * | 9/2001 | Marino | 623/17.11 |
| 6,332,984 | B1 | 12/2001 | Boyd et al. | |
| 6,375,682 | B1 | 4/2002 | Fleischmann et al. | |
| 6,395,031 | B1 | 5/2002 | Foley et al. | |
| 6,419,705 | B1 * | 7/2002 | Erickson | 623/17.16 |
| 6,527,804 | B1 | 3/2003 | Gauchet et al. | |
| 6,533,817 | B1 | 3/2003 | Norton et al. | |
| 6,632,235 | B2 | 10/2003 | Weikel et al. | |
| 6,733,532 | B1 | 5/2004 | Gauchet et al. | |
| 6,827,743 | B2 * | 12/2004 | Eisermann et al. | 623/23.54 |
| 6,835,205 | B2 * | 12/2004 | Atkinson et al. | 623/17.11 |
| 6,981,989 | B1 | 1/2006 | Fleischmann et al. | |
| 6,984,246 | B2 | 1/2006 | Huang | |
| 7,166,131 | B2 * | 1/2007 | Studer et al. | 623/17.16 |
| 7,563,284 | B2 | 7/2009 | Coppes et al. | |
| 7,708,778 | B2 | 5/2010 | Gordon et al. | |
| 7,828,846 | B2 * | 11/2010 | Biedermann et al. | 623/17.13 |
| 7,862,618 | B2 | 1/2011 | White et al. | |
| 7,901,409 | B2 * | 3/2011 | Canaveral et al. | 606/86 R |
| 7,918,875 | B2 * | 4/2011 | Lins et al. | 606/248 |
| 8,070,813 | B2 * | 12/2011 | Grotz et al. | 623/17.11 |
| 8,105,382 | B2 * | 1/2012 | Olmos et al. | 623/17.15 |
| 8,206,447 | B2 * | 6/2012 | de Villiers et al. | 623/17.14 |
| 8,257,440 | B2 * | 9/2012 | Gordon et al. | 623/17.15 |
| 8,273,124 | B2 | 9/2012 | Renganath et al. | |
| 8,613,768 | B2 * | 12/2013 | Biedermann et al. | 623/17.14 |
| 2003/0009226 | A1 | 1/2003 | Graf | |
| 2003/0171813 | A1 * | 9/2003 | Kiester | 623/17.11 |
| 2004/0133280 | A1 * | 7/2004 | Trieu | 623/17.16 |
| 2004/0260396 | A1 | 12/2004 | Ferree et al. | |
| 2005/0033437 | A1 | 2/2005 | Bao et al. | |
| 2005/0143821 | A1 | 6/2005 | Zdeblick et al. | |
| 2005/0192671 | A1 | 9/2005 | Bao et al. | |
| 2006/0052871 | A1 * | 3/2006 | Studer et al. | 623/17.13 |
| 2006/0142861 | A1 | 6/2006 | Murray | |
| 2006/0149279 | A1 | 7/2006 | Mathews | |
| 2006/0241632 | A1 | 10/2006 | Sherman et al. | |
| 2006/0241765 | A1 | 10/2006 | Burn et al. | |
| 2006/0293749 | A1 | 12/2006 | Hudgins et al. | |
| 2007/0050032 | A1 * | 3/2007 | Gittings et al. | 623/17.12 |
| 2007/0093901 | A1 | 4/2007 | Grotz et al. | |
| 2007/0173940 | A1 * | 7/2007 | Hestad et al. | 623/17.12 |
| 2007/0219634 | A1 * | 9/2007 | Greenhalgh et al. | 623/17.16 |
| 2007/0233254 | A1 * | 10/2007 | Grotz et al. | 623/17.11 |
| 2008/0058931 | A1 | 3/2008 | White et al. | |
| 2008/0154382 | A1 * | 6/2008 | de Villiers et al. | 623/17.16 |
| 2008/0288073 | A1 | 11/2008 | Renganath et al. | |

OTHER PUBLICATIONS

International Search Report for PCT/US08/61858, Sep. 22, 2008 (1 page.).

* cited by examiner

SELF-DISTRACTING CAGE

CROSS-REFERENCE TO RELATED APPLICATIONS

The present application is a divisional of U.S. application Ser. No. 11/750,113, filed May 17, 2007, and entitled "Self-Distracting Cage," and now issued as U.S. Pat. No. 8,273,124, on Sep. 25, 2012, the disclosure of which is incorporated herein by reference in its entirety.

FIELD OF THE INVENTION

The present invention relates to methods and devices for spinal stabilization and fusion, and particularly to an expandable intervertebral implant.

BACKGROUND OF THE INVENTION

A leading cause of lower back pain arises from lumbar intervertebral disc pathology caused by degeneration of the intervertebral disc. As a disc degenerates, the nucleus and annulus functions are compromised. The nucleus becomes thinner and unable to handle compression loads. The annulus fibers become redundant as the nucleus shrinks. The redundant annular fibers are less effective in controlling vertebral motion. The disc pathology can result in the bulging of the annulus into the spinal cord or nerves, narrowing of the space between the vertebra where the nerves exit, tears of the annulus under abnormal loads caused by excessive motion between the vertebra, and disc herniation. Additionally, lower back pain may be caused by collapse of the disc and the dysarthrosis of an unstable or degenerative vertebral facet joint. A technique for managing these problems is to remove the problematic disc and replace it with a porous intervertebral fusion device that restores disc height and allows for bone growth therethrough for the fusion of the adjacent vertebra.

In general, delivery of conventional intervertebral fusion devices requires significantly invasive implantation procedures. In some configurations, the intervertebral implants are not adjustable by the surgeon during an open surgical procedure. Therefore, the surgeon must choose the size that most closely matches the desired height, length, and width dimensions, and then make the implant fit. Because these implants are of a predetermined size and shape, the implant site must correspond to the implant configuration. This can require extensive site preparation to complete implantation. Fusion devices with parallel superior and inferior surfaces either fit tightly posteriorly and loosely anteriorly, or require removal of vertebral bone in order to fit posteriorly. Extensive site preparation such as this can compromise the success of the implantation procedure by causing excessive damage to the receiving vertebral elements. In addition, open surgical implantation of posterior implants requires excision of stabilizing muscles, ligaments, tendons, and bony structures such as facet joints. The implants must therefore overcome the destabilization caused by the surgery, as well as provide additional stabilization to promote bony fusion. In addition, open anterior surgery in the lumbar spine can present risks due to the close proximity of the aorta and bifurcation of the aorta.

To combat some problems associated with open anterior surgeries, minimally invasive procedures have been developed. Current implants, or inner body cages, used in minimally invasive procedures, however, are still unable to conform to the necessary lordotic angle between adjacent vertebra. In addition, surgeons must rely on high manual forces to distract (dilate) the disc space. Finally, current cages do not have a shape that is optimal in terms of support.

Accordingly, there is a need for instrumentation and techniques that allow for a self-distracting, self-leveling, and adjustable inner body cage that can be easily inserted and positioned.

SUMMARY OF THE INVENTION

The present invention provides various spinal implants and methods for stabilizing the spine. In one exemplary embodiment, a spinal implant is provided having an expandable container with an interior volume that is selectively expandable between a compressed condition and an expanded condition. The expandable container is coupled to a superior endplate member having a bone-contacting surface and an engagement surface effective to mate with a superior surface of the expandable container and an inferior endplate member having a bone-contacting surface and an engagement surface effective to mate with an inferior surface of the expandable container. In addition, at least one inlet port is formed in the expandable container and is effective to communicate a fluid to at least one cavity disposed within the interior volume of the expandable container.

While the implant can have a variety of configurations, in one exemplary embodiment, the implant can include an angular adjustment mechanism configured to enable continuously variable angular adjustment of the superior and inferior endplate members with respect to a plane extending horizontally therethrough. For example, the angular adjustment mechanism can include an articulating pleated member, such as a bellows, which extends between the superior and inferior endplate members. Alternatively, the angular adjustment mechanism can include an articulating joint, such as a ball joint, disposed within one of the superior and inferior endplate members.

In another aspect of the invention, the implant can include a continuously variable height adjustment mechanism, such as a hydraulic mover. In an exemplary embodiment, the hydraulic mover can be a curable material, an expandable balloon, and/or a piston.

While the implant can have many different sizes, in one exemplary embodiment, the expandable container and the superior and inferior endplate members have a combined minimum height of about 5 mm in the compressed condition and a combined maximum height of about 15 mm in the expanded condition.

In a further aspect of the invention, the superior and inferior endplate members are rigid and can include a biocompatible elastomeric component. In an exemplary embodiment, the elastomeric component can be curable polymers, semi-rigid hydrogels, high-durometer silicones or polyurethanes.

The invention also relates to methods for distracting two adjacent vertebrae. In one embodiment, the method can include surgically delivering a selectively expandable spinal fusion implant into an intervertebral disc space. The implant can then be expanded until a superior endplate and an inferior endplate of the spinal implant contact opposing bony surfaces of the two adjacent vertebrae and adjustments can be made to the expansion of the implant until the two adjacent vertebrae are at a desired separation.

The methods disclosed herein are particularly well suited for a minimally invasive surgical procedure in which the spinal fusion implant is delivered through an access port or a cannula. In one exemplary method, the minimally invasive surgical procedure is conducted while the implant is at a compressed height of about 5 mm. Once positioned between the vertebra, the implant can be selectively expanded to any height appropriate for the intervertebral disc space. Additionally, angular adjustments can be made to the superior and inferior endplates with respect to a plane extending horizontally therethrough to better conform to a natural lordotic angle of the intervertebral disc space.

These and other aspects of the presently disclosed embodiments will be described in detail below.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, the presently disclosed embodiments relate to methods for simultaneously distracting two adjacent vertebral bodies and to spinal implants configured for self-distraction of the intervertebral disc space. In particular, the self-distracting spinal implants disclosed herein are incrementally adjustable for height and for lordotic angle. In one embodiment, the implant is of an optimal shape for placement within the intervertebral disc space and is configured to replicate and restore a natural angle between two adjacent vertebrae. In another embodiment, the implant is configured to contain a bone packing material to encourage bony ingrowth between two adjacent vertebrae.

In one exemplary embodiment, a spinal implant is provided having an expandable container with an interior volume that is selectively expandable between a compressed condition and an expanded condition. The expandable container is disposed between a superior endplate member having a bone-contacting surface and an engagement surface effective to mate with a superior surface of the expandable container and an inferior endplate member having a bone-contacting surface and an engagement surface effective to mate with an inferior surface of the expandable container. In addition, at least one inlet port is formed in the expandable container and is effective to communicate a fluid to at least one cavity disposed within the interior volume of the expandable container.

Figure 1A:
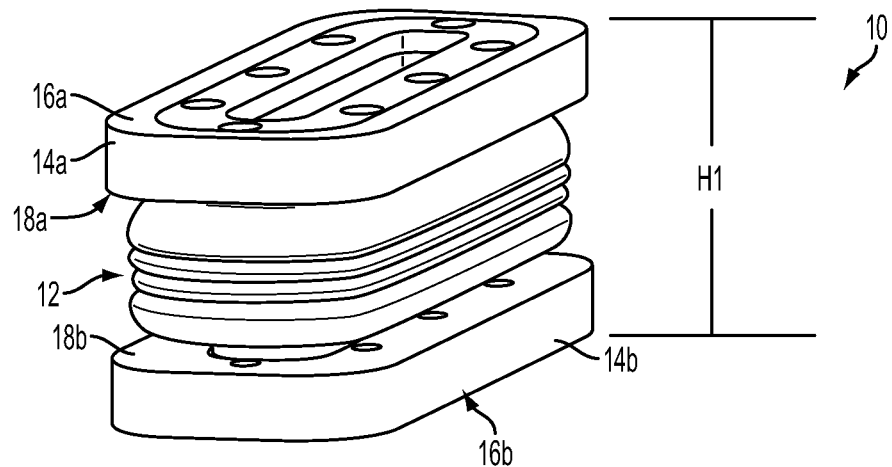
FIG. 1A is a perspective view of a self-distracting spinal implant in a compressed condition.
Figure 1B:
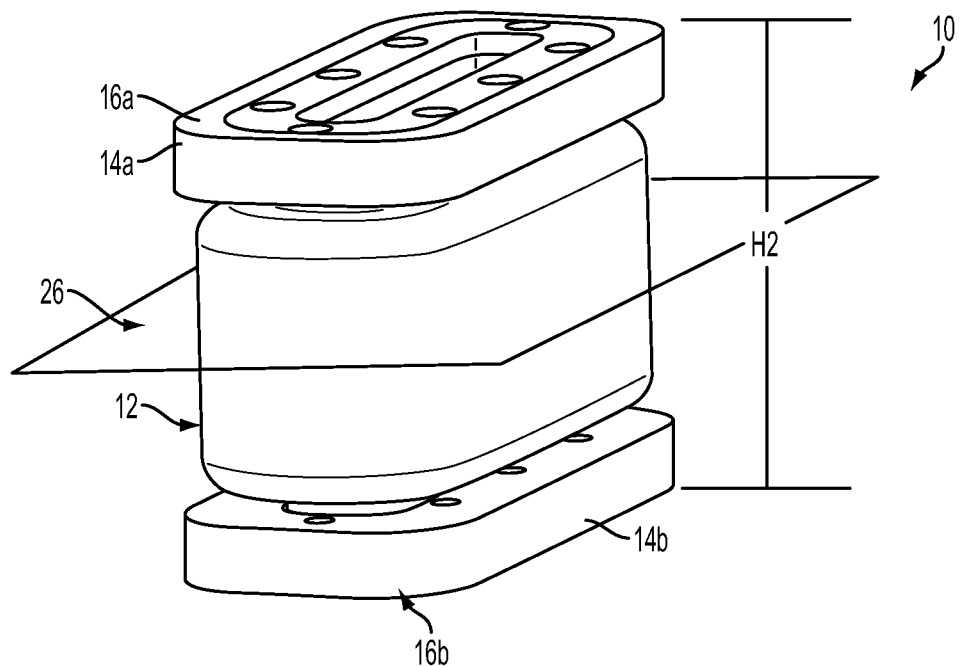
FIG. 1B is a perspective view of the implant of FIG. 1A in an expanded condition.

FIGS. 1A and 1B illustrate one embodiment of a self-distracting implant 10 having a pleated member 12, such as an articulating bellows, disposed between a superior endplate member 14a and an inferior endplate member 14b. The implant 10 can have a variety of shapes and sizes, but in one embodiment, the implant 10 can be elliptically shaped and it has a distraction envelope in the range of about 5 mm to 15 mm. FIG. 1A shows the implant 10 in a compressed condition, in which a height H1 is at a minimum of the compression envelope, e.g., about 5 mm. FIG. 1B shows the implant 10 in an expanded condition, in which a height H2 is at a maximum envelope, e.g., about 15 mm.

In the embodiment illustrated in FIGS. 1A and 1B, the superior endplate member 14a includes a superior bone-contacting surface 16a and an inferior engagement surface 18a that is configured to mate with a superior surface of the pleated member 12. The inferior endplate member 14b likewise includes an inferior bone-contacting surface 16b and a superior engagement surface 18b that is configured to mate with an inferior surface of the pleated member 12. The endplate members 14a, 14b are substantially rigid and can be formed from a variety of known biocompatible materials, including carbon fiber reinforced polymer (CFRP), metal, and any metal alloys. In one exemplary embodiment, the superior and inferior bone-contacting surfaces 16a, 16b are configured to seat and retain a formable component (not shown) that can conform to the natural contours of the adjacent vertebra to enhance the fit within the intervertebral disc space. A person skilled in the art will realize that any appropriate biocompatible formable component known in the art can be used to improve the conformance of the superior and inferior endplate members 14a, 14b. Suitable examples include high-durometer silicones and polyurethanes, in-situ curing resins such as polymethylmethacrylate (PMMA) (e.g., SmartSet GMV™ by DePuy Orthopedics of Warsaw, Ind.)

and tetraethyleneglycol dimethacrylate (TEGDMA) (e.g., NRC™ by Dentsply of York, Pa.), curing/setting calcium phosphate cements (e.g., NanOss™ Bone Void Filler by Angstrom Medica of Woburn, Mass.), polyanhydrides, polyvinyl acetates, and polysaccharides (e.g., Eureka™ DUET by SurModics of Eden Prairie, Minn.).

As shown in FIG. 1A, when the implant 10 is in the compressed condition, the superior and inferior endplate members 14a, 14b can be parallel to one another and to a horizontal plane 26 extending through the implant. Because the endplate members 14a, 14b are attached to the pleated member 12, however, their angle with respect to each other and with respect to the horizontal plane 26 can be adjusted. As the implant 10 is expanded, the endplate members 14a, 14b are free to rotate with respect to the horizontal plane 26 as necessary to compensate for any height differences in the implant 10 and any necessary lordotic angle within the intervertebral disc space. The pleated member 12 coupled with the endplate members 14a, 14b can allow for a lordotic angle of any where between zero and at least sixteen degrees with respect to the horizontal plane 26 extending therethrough. This allows the endplate members 14a, 14b to better conform to any necessary or natural lordotic angle between two adjacent vertebrae.

FIGS. 2A-2D illustrate one example of a pleated member 12 that can be used to form the implant 10 of the type described above. In one embodiment, the pleated member 12 is expandable and compressible as needed, having relatively thin walls with a flexible bellows-like structure. The pleated member 12 can be formed from any suitable material known in the art. Some examples of suitable materials include elastomeric materials, polymeric materials, metals, and metal alloys.

Figure 2A:
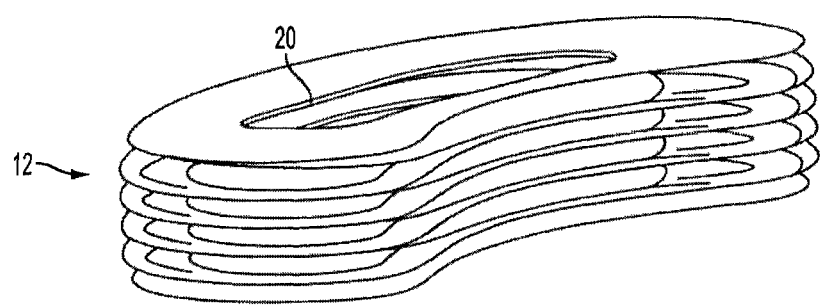
FIG. 2A is a perspective view of a free-standing pleated member for use with a self-distracting spinal implant.
Figure 2B:
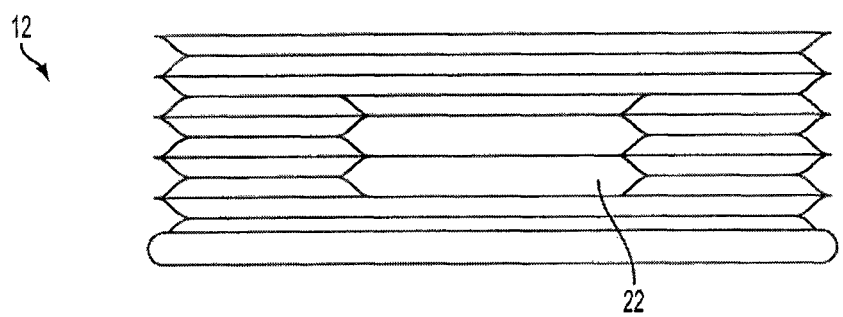
FIG. 2B is a front view of the pleated member of FIG. 2A in the compressed condition, showing an inlet port.
Figure 2C:
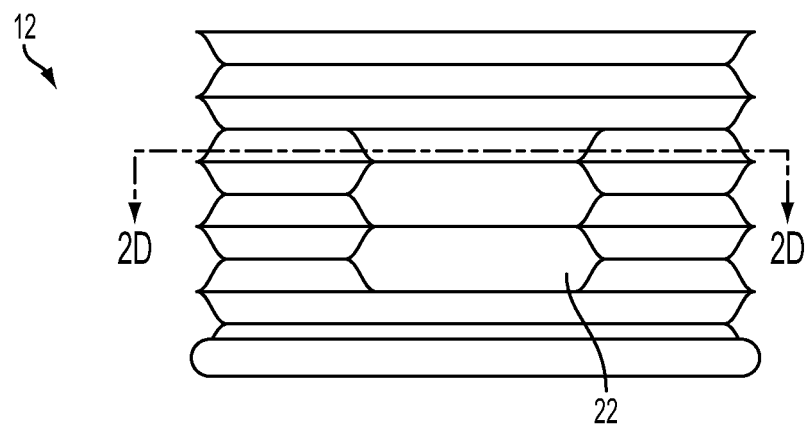
FIG. 2C is a front view of the pleated member of FIG. 2A, in the expanded condition.
Figure 2D:
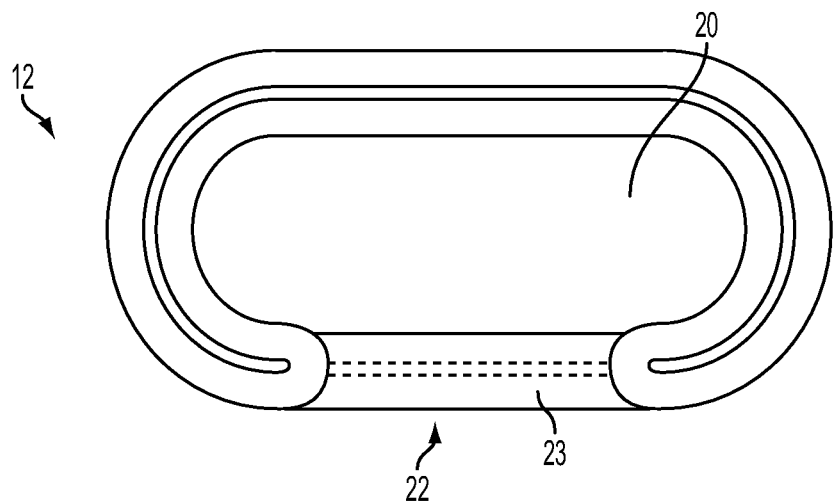
FIG. 2D is a top sectional view of the pleated member of FIG. 2A, showing an interior volume.

As shown most clearly in FIG. 2D, an interior volume 23 can be disposed within the pleated member 12 and is configured for receiving a compressible and curable expansion material which enables the pleated member 12 to be expanded as needed. In the alternative, an inner annular opening 20 of the pleated member 12 can contain an expandable balloon (not shown), also configured for receiving an expansion material. Any suitable compressible and curable expansion material known in the art can be used to fill the interior volume 23 or the expandable balloon. Some examples of suitable materials include polymethyl methacrylate (PMMA), synthetic cortical bone fillers such as setting/curing calcium phosphate cement (e.g., Cortoss™), tetraethyleneglycol dimethacrylate (Bis-Teg DMA), polyurethane, cyanoacrylate, etc. A person skilled in the art will appreciate that any biocompatible, expandable balloon known in the art can be used within the inner annular opening 20 of the pleated member 12.

In another exemplary embodiment, the interior volume 23 within the pleated member 12 can contain more than one cavity or chamber suitable for an expansion material, or alternatively, for multiple expandable balloons. Having more than one chamber within the interior volume 23 will allow for greater flexibility in height and angle customization. For example, one chamber can be filled to a greater extent than another chamber, thereby causing one part of the pleated member 12 to expand to a height greater than another part of the pleated member 12. In addition, one chamber can contain an expandable balloon which is expanded to a greater extent than an expandable balloon within a second chamber. This would allow the implant 10 to be appropriately configured for a more natural lordotic angle within the intervertebral disc space. A person skilled in the art will appreciate that any number of chambers and/or expandable balloons can be used with the pleated member 12 so that the height and angle of the implant 10 is completely customizable.

FIGS. 2B-2D also illustrate an inlet port 22 formed in the pleated member 12 which is effective to communicate a fluid to the interior volume 23 of the pleated member 12. In the case where a curable expansion material is used to expand the implant 10, a filler device can be attached to and detached from the inlet port 22 via a snap off connector, a natural hinge, a luer connector, a notch sensitive device, or any other connection mechanism known in the art. In the case where an expandable balloon is used with the pleated member 12, the mouth or inlet of the balloon can be congruent with the inlet port 22 so that a filler device attached to the inlet port 22 is effective to fill the expandable balloon. Alternatively, the filler device can enter through the inlet port 22 and attach directly to the balloon within the interior volume 23 of the implant for filling purposes. A person skilled in the art will appreciate that any filler device known in the art can be used to fill the interior volume 23 and/or expandable balloon with a curable expansion material. Although inlet port 22 is shown to be disposed within a side of the pleated member 12, one skilled in the art will appreciate that it can alternatively be disposed within the superior or inferior endplate members 14a, 14b.

In an exemplary embodiment in which multiple connected chambers are used within the interior volume of the pleated member 12, a person skilled in the art will appreciate that flow restrictors can be used between the chambers to allow different quantities of material to be injected into different areas of the implant. Additionally or alternatively, the flow rate restrictors can allow material to be injected at different flow rates. Such a design facilitates customization of height and lordotic angle. Alternatively, multiple inlet ports disposed within the sides of the pleated member 12 and/or the endplate members 14a, 14b can be used to fill independent multiple chambers or multiple expandable balloons.

Figure 3A:
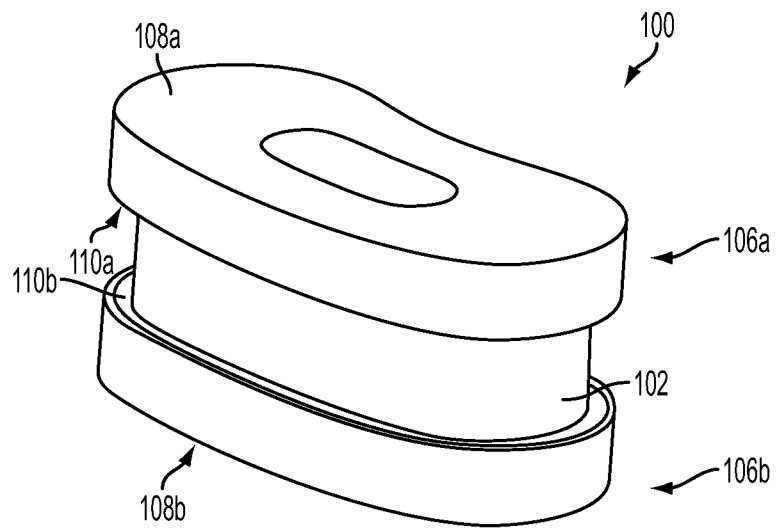
FIG. 3A is a perspective view of a hard-walled, self-distracting spinal implant in a piston configuration, in the compressed condition.
Figure 3B:
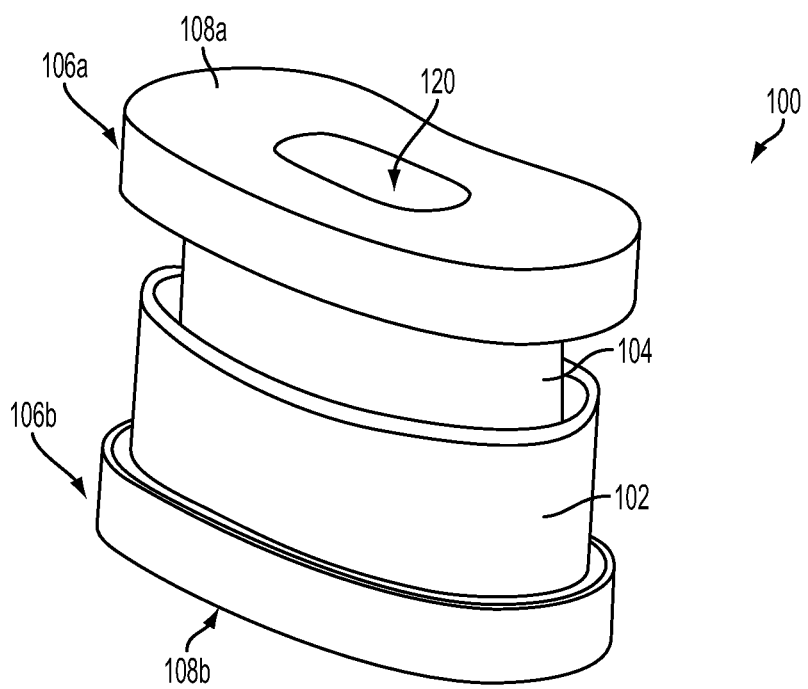
FIG. 3B is a perspective view of the implant of FIG. 3A in the expanded condition.
Figure 3C:
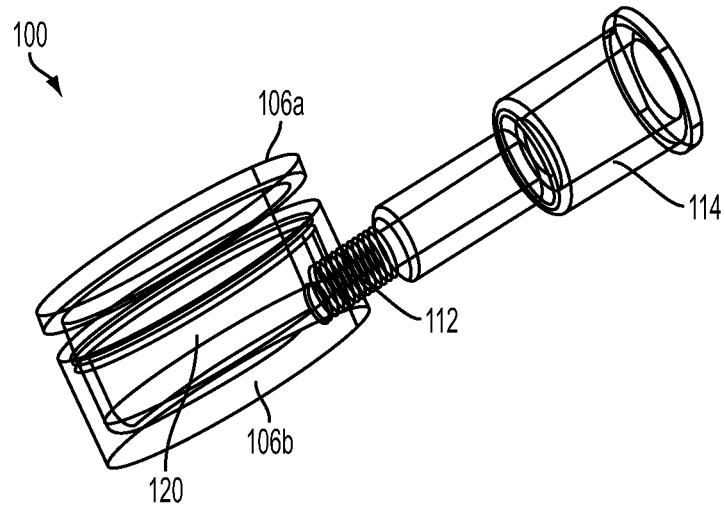
FIG. 3C is a perspective view of the implant of FIG. 3A, showing a hydraulic tool attached.

The self-distracting spinal implants disclosed herein can be in a variety of shapes, and FIGS. 3A and 3B show one exemplary embodiment of an elliptical or cashew-shaped, hard-walled implant 100 having a fixed platen member 102 and a movable platen member 104 in a piston-like configuration. At least a portion of the movable platen member 104 is disposed within the fixed platen member 102 and the two are slidingly engaged with one another in a fluid tight seal. A superior endplate member 106a includes a superior bone-contacting surface 108a and an inferior engagement surface 110a that is configured to mate with a superior surface of the movable platen member 104. An inferior endplate member 106b includes an inferior bone-contacting surface 108b and a superior engagement surface 110b that is configured to mate with an inferior surface of the fixed platen member 102. As shown an inner annular opening 120 may extend through the device. FIG. 3C shows the implant 100 in a compressed condition, with an inlet port 112 disposed in a side of the fixed platen member 102. The inlet port 112 is in fluid communication with an interior volume 123' (FIG. 3D) that is configured for receiving a hydraulic fluid, which can be delivered through any suitable filler device, such as a hydraulic feed 114.

Figure 3D:
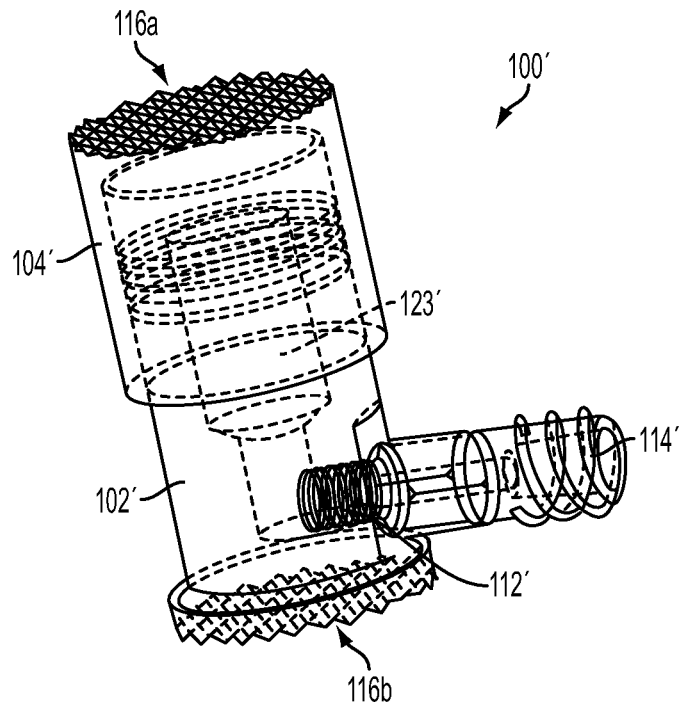
FIG. 3D is a perspective view of an implant of the type shown in FIG. 3A in an alternate, round shape showing a hydraulic tool attached.

FIG. 3D shows a similarly constructed implant 100' in a piston-like configuration, as described above, having a circular configuration. An inlet port 112' located in the fixed platen member 102' is provided, and is configured to receive a hydraulic feed 114'. The inlet port 112' is in fluid communication with an interior volume 123' and is configured to receive a hydraulic fluid, which can be a curable material. FIG. 3D also illustrates that the superior and inferior bone-contacting surfaces 116a, 116b of the implant 100' include a roughened surface. The roughened surface allows the implant 100' to have a more stable fit within the intervertebral disc space by providing increased friction between the vertebral endplates and the implant 100'. A person skilled in the art will appreciate that any of the implant embodiments disclosed herein can include bone-contacting surfaces formed from any roughened surface known in the art. A person skilled in the art will also appreciate that any of the embodiments disclosed herein can be formed of any geometrical shape.

As shown in FIGS. 3C and 3D, the hydraulic feed 114, 114', or a similar device, is configured to communicate a fluid to the interior volume 123' of the piston and thereby cause the movable platen member 104, 104' to move relative to the fixed platen member 102, 102' to expand and increase the height of the implant 100, 100'. A person skilled in the art will appreciate that an inlet port capable of receiving a hydraulic feed can also be formed in either of the superior and inferior endplate members.

Figure 4A:
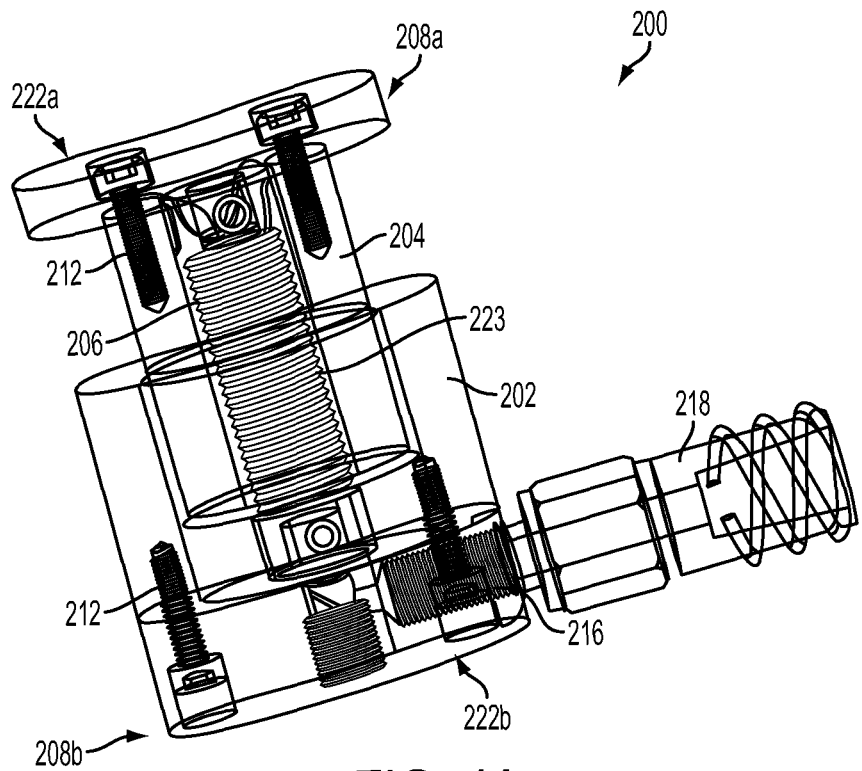
FIG. 4A is a perspective view of a self-distracting spinal implant in a piston configuration with a pleated member.
Figure 4B:
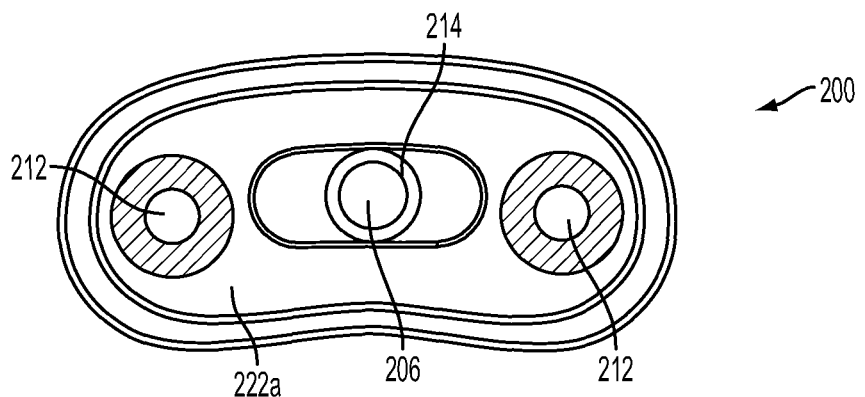
FIG. 4B is a top view of the implant of FIG. 4A.

FIGS. 4A and 4B show a further embodiment of a self-distracting spinal implant 200 having an elliptical or cashew-shape and including a fixed platen member 202 and a movable platen member 204. At least a portion of the movable platen member 204 is disposed within the fixed platen member 202 in a piston-like configuration with a fluid tight seal therebetween. A pleated member 206 is contained in a bore 214 formed within the movable platen member 204 such that extends between a superior endplate member 208a and an inferior endplate member 208b. The pleated member 206 is configured to receive a hydraulic fluid (e.g., a curable material) for moving the piston. The pleated member 206 provides more flexibility in the tolerance required for this fluid tight seal than if the fixed platen member 202 were mated directly to the movable platen member 204 without the pleated member 206. As shown in FIG. 4A, the superior and inferior endplate members 208a, 208b are otherwise coupled to the movable platen member 204 and the fixed platen member 202, respectively, by biocompatible screws 212. The screws 212 can be inserted into the superior and inferior endplate members 208a, 208b through a superior bone-contacting surface 222a and an inferior bone-contacting surface 222b. A person skilled in the art will appreciate that any appropriate method of attaching the superior and inferior endplate members 208a, 208b to the movable platen member 204 and the fixed platen member 202 can be used.

In the illustrated embodiment, an inlet port 216 is disposed in the fixed platen member 202 of the implant 200 and is in fluid communication with an interior volume 223 of the piston, which is configured for receiving hydraulic fluid. Fluid is injected into the implant 200 via the inlet port 216 and a hydraulic feed 218 to cause the movable platen member 204 and the pleated member 206 to move relative to the fixed platen member 202 to expand and increase the height of the implant 200. FIG. 4A shows the implant 200 in an expanded condition.

Figure 5A:
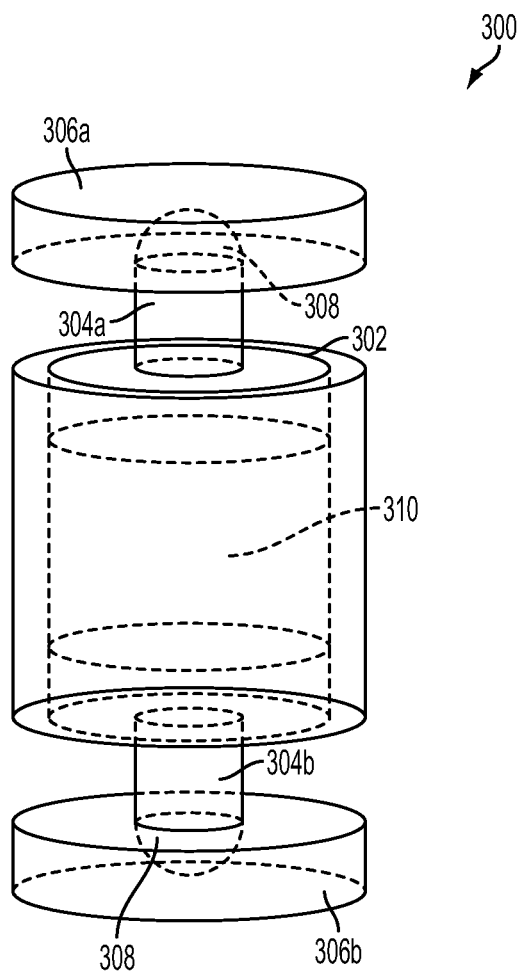
FIG. 5A is a front view of a self-distracting spinal implant in a piston configuration with articulating joints.
Figure 5B:
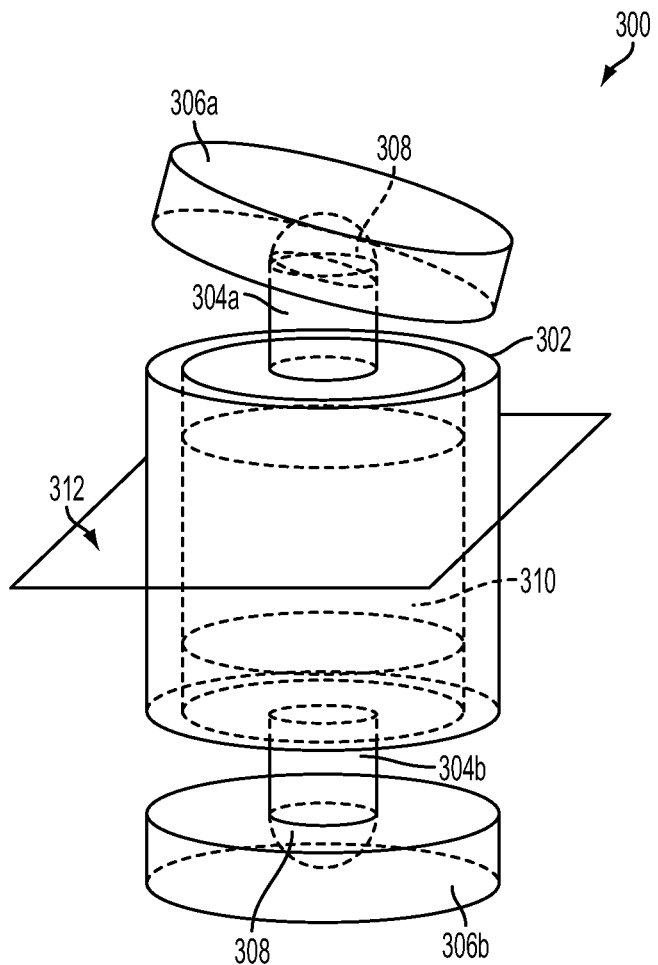
FIG. 5B is a front view of the implant of FIG. 5A showing one end plate oriented at an angle.

FIGS. 5A and 5B show another exemplary embodiment of a self-distracting spinal implant 300 having two piston members and two articulating joints. A first piston member includes a fixed platen member 302 and a superior movable platen member 304a disposed within a superior portion of the fixed platen member 302 in a piston-like configuration with a fluid tight seal. A second piston member likewise includes the fixed platen member 302, as well as an inferior movable platen member 304b disposed within an inferior portion of the fixed platen member 302 in a piston-like configuration with a fluid tight seal.

In the illustrated embodiment, the superior movable platen member 304a is connected to a superior endplate member 306a via an articulating joint 308, such as a ball joint, that enables angulation of the superior endplate member 306a. The inferior movable platen member 304b is likewise connected to an inferior endplate member 306b via an articulating member 308. In an expanded condition, the superior and/or inferior endplate members 306a, 306b can rotate via the articulating joint 308 relative to a horizontal plane 312 extending therethrough, as illustrated in FIG. 5B. This allows the implant 300 to conform to any necessary and/or natural lordotic angle within the intervertebral disc space. A person skilled in the art will appreciate that an inlet port can be formed in the fixed platen member 302 of the implant 300, as well as in any other portion of the implant 300. The inlet port can be configured to receive a hydraulic feed capable of communicating hydraulic fluid to an interior volume 310 of the implant. The hydraulic fluid is effective to move the superior and inferior movable platen members 304a, 304b relative to the fixed platen member 302, thereby expanding and retracting the implant 300 as necessary.

Figure 6A:
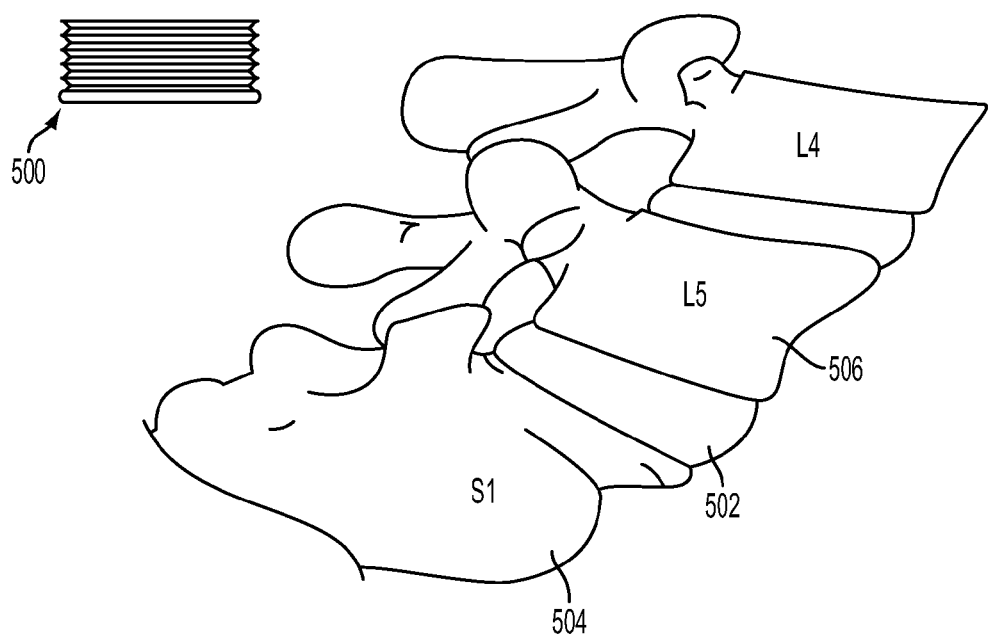
FIG. 6A is a representation of a self-distracting spinal implant before it is compressed for insertion into an intervertebral disc space.
Figure 6B:
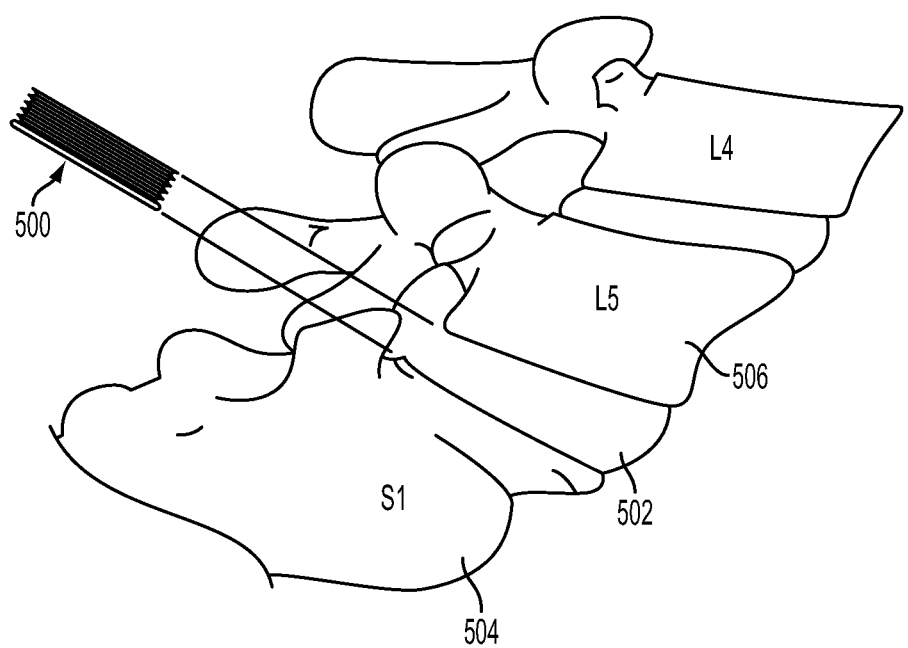
FIG. 6B is a representation of the implant of FIG. 6A in the compressed condition for insertion in the intervertebral disc space.
Figure 6C:
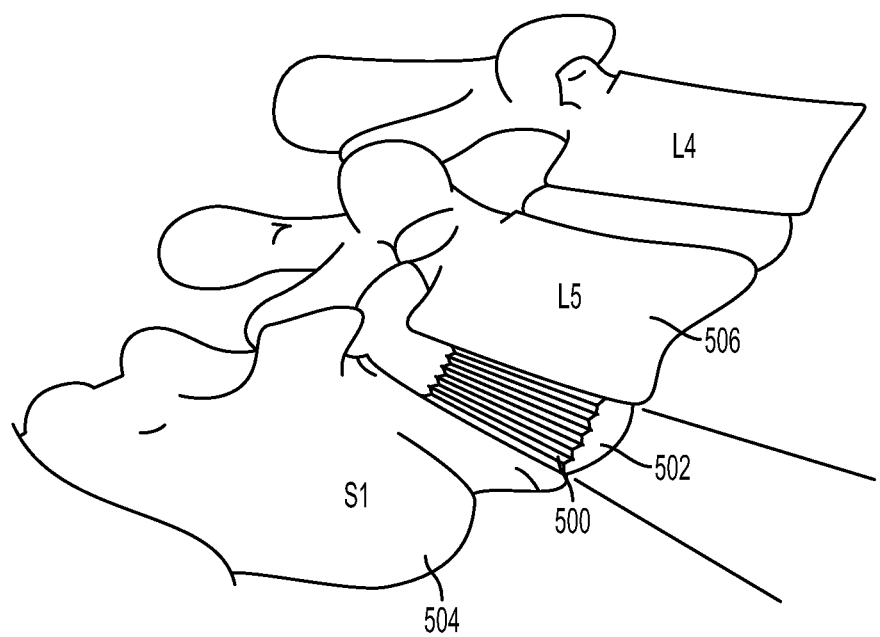
FIG. 6C is a representation of the implant of FIG. 6A in the expanded condition after it is inserted into the intervertebral disc space.

In use, a variety of surgical techniques, including conventional open surgery and minimally invasive surgery, can be used to place an exemplary self-distracting implant within the intervertebral disc space. Referring to FIGS. 6A-6C, in one exemplary method, the implant 500 can be inserted into the intervertebral disc space 502 via an access port or cannula that extends through a patient's skin to a site where the implant is to be implanted. As shown in FIG. 6B, the implant 500 will initially be in a compressed condition with a minimal height, for example, of about 5 mm. After placement within the disc space 502, the implant 500 can be expanded to distract two adjacent vertebrae 504, 506 by an appropriate amount up to the implant's maximum height, for example, of about 15 mm. After distraction, any necessary angular adjustments can be made so that the implant 500 conforms to the natural lordotic angle and spacing between the adjacent vertebrae 504, 506, as shown in FIG. 6C.

In another exemplary method involving the implant 10 illustrated in FIGS. 1A and 1B, the implant 10 can be inserted through a cannula or port and into a disc space in a compressed condition with a minimum height of about 5 mm. A compressible and curable expansion material such as PMMA, synthetic cortical bone fillers, such as calcium phosphate cement (e.g., Cortoss™), tetraethyleneglycol dimethacrylate (Bis-Teg DMA), polyurethane, cyanoacrylate, polysaccharides, polyanhydride, in situ curing silicone, etc., is then injected into the interior volume, multiple chambers, or expandable balloon of the pleated member 12 by a filler device. As the material is injected, the superior and inferior endplate members 14a, 14b move apart upon expansion of the pleated member 12 so that they contact and apply a distraction force to the two adjacent vertebrae, causing them to distract. The filler material is injected into the interior volume until the vertebrae are at a desired separation. The pleated member 12 allows the implant 10 to conform to a natural lordotic angle as it expands. After the necessary height and angle are achieved, the material can be quickly cured by light or chemical so that the material forms a solid plug within the implant 10, thereby retaining the customized height and lordotic angle. A person skilled in the art will appreciate that any biocompatible, compressible, and curable material known in the art can be injected into the implant 10 to distract the vertebrae. A person skilled in the art will also appreciate that the implant 10 can be expanded to any height within its distraction envelope of between about 5 mm and 15 mm.

In another exemplary method involving use of the implants illustrated in FIGS. 3A-3D and in FIGS. 4A-4B, the implant 100, 200 is inserted into a disc space in a compressed condition with a minimum height of about 5 mm. A hydraulic fluid (which can be curable) is then injected into the interior volume 123', 223 of the piston via the hydraulic feed. The movable platen member 104, 204 moves relative to the fixed platen member 102, 202 to cause the implant 100, 200 to expand. The superior and inferior bone-contacting surfaces exert a pressure on the adjacent vertebrae, causing them to distract. The surgeon can thereby adjust the spacing between the adjacent vertebrae by adjusting the height of the implant 100, 200 up to its maximum height of about 15 mm. When the desired spacing between the vertebrae has been achieved, the hydraulic feed can be removed (and cured in the case of a curable material), and the implant 100, 200 will remain at the desired height, providing support and stabilization between the vertebrae.

In a further exemplary method involving the use of the implant 300 illustrated in FIGS. 5A and 5B, the implant 300 is inserted within a disc space in a compressed condition with a minimum height of about 5 mm. A hydraulic fluid (which can be curable) is then injected into the interior volume 310 of the piston via the hydraulic feed. The superior and inferior movable platen members 304a, 304b move relative to the fixed platen member 302 to cause the implant 300 to expand. The superior and inferior bone-contacting surfaces thus exert a pressure on the adjacent vertebrae, causing them to distract as the implant 300 is expanded. The surgeon can thereby adjust the spacing between the adjacent vertebrae by adjusting the height of the implant 300 up to its maximum height of about 15 mm. In addition, the surgeon can make angular adjustments to the superior and/or inferior endplate members 306a, 306b via the articulating joints 308 relative to the horizontal plane 312 so that the implant 300 better conforms to the necessary and/or natural lordotic angle between the adjacent vertebra. When the desired spacing and angle between the vertebrae has been achieved, the hydraulic feed can be removed (and cured in the case of a curable material), and the implant 300 will remain at the desired height and angle, providing support and stabilization between the vertebrae.

In still another exemplary method, a person skilled in the art will appreciate that multiple pistons can be used in combination with multiple pleated members within one implant to obtain height customization as well as angle customization within the intervertebral disc space. After the implant is inserted in a compressed condition, each piston member can be independently adjusted to achieve different heights, which allows the implant to conform to any necessary or natural lordotic angle of the disc space. The pleated members are configured for receiving a hydraulic fluid and provide flexibility in the tolerance required for the fluid tight seal that exists between a movable platen member of each of the multiple pistons and a superior endplate member. A hydraulic feed can be used to activate the pistons and can be removed once the required height and angle of the implant has been achieved.

Figure 7A:
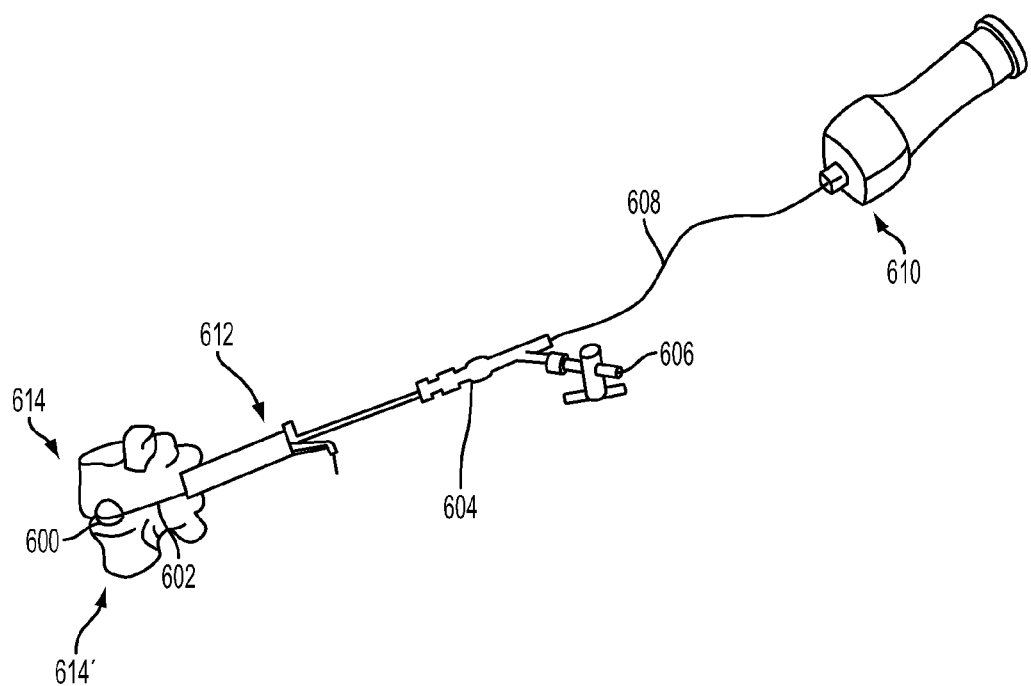
FIG. 7A is a representation of a system for inserting a self-distracting spinal implant into an intervertebral disc space.
Figure 7B:
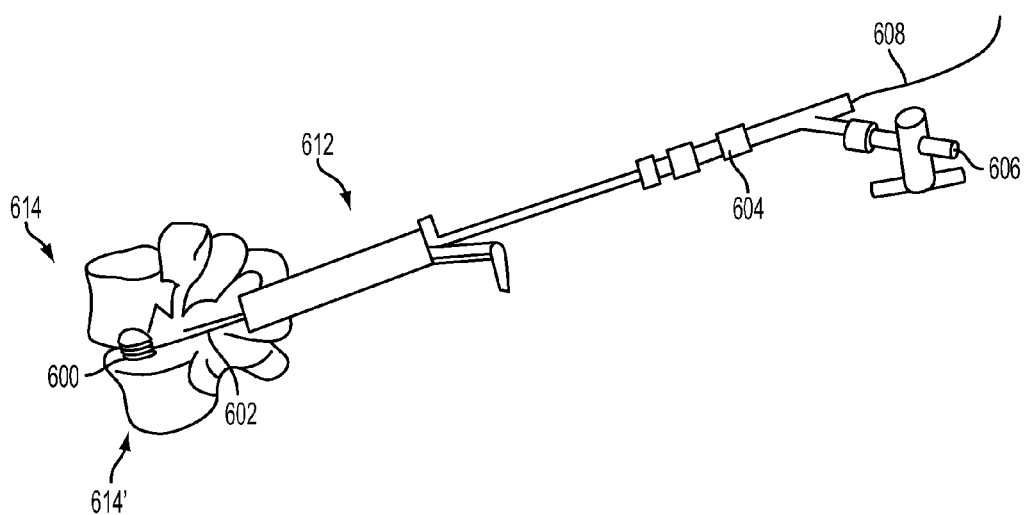
FIG. 7B is a representation of the system of FIG. 7A.

Referring now to FIGS. 7A and 7B, another exemplary method for inserting a self-distracting spinal implant will be discussed. In the illustrated embodiment, a system is pre-assembled to include a self-distracting spinal implant 600 attached to an insertion tool, such as a cannula 602. As shown, a liquid feed device 604 is in fluid communication with the cannula 602 to inject a curable expansion material into the implant 600. A fluid control valve 606 is disposed on a proximal end of the liquid feed device 604 so that the flow of the curable expansion material can be controlled. In addition, a fiber optic cable 608 is disposed within the cannula 602 and its distal end extends into an inlet port of the implant 600 to facilitate curing of the injected material. The fiber optic cable 608 can be attached at its proximal end to any suitable source of curing energy, such as a high intensity light-emitting diode (LED) disposed within a housing 610 as shown in FIG. 7B.

In use, the implant 600 is attached to a distal end of the cannula 602 and is initially in a compressed condition with a height, for example, of about 5 mm. Using the cannula 602, the implant 600 is inserted through a minimally invasive surgery access port 612 that extends through a patient's skin to a site where the implant is to be implanted, and which can be located adjacent to the relevant vertebral bodies 614, 614'. The implant 600 is maneuvered into the intervertebral disc space with the cannula 602. Once in place, the fluid control valve 606 is opened to allow a curable expansion material to flow through the cannula 602 and into the interior volume of the implant 600. As the fluid is injected, the implant 600 expands and causes the distraction of the adjacent vertebrae 614, 614' to any height up to the implant's maximum height of about 15 mm. By maneuvering the implant 600 and adjusting the fluid flow of the curable material, a surgeon can then make any necessary adjustments to the distraction space and the relative force of the implant 600 on the vertebrae 614, 614'. In addition, angular adjustments can be made to the implant 600 to compensate for any required lordotic angle between the vertebrae 614, 614'. Once these adjustments have been made, the curing energy can be activated to essentially instantaneously cure the material within the implant 600, forming a solid plug that will retain the height and angular requirements of the disc space. The cannula 602 can then be removed from the implant 600, for example, by breaking or snapping a notch attachment. A person skilled in the art will appreciate that the cannula 602 can be joined to and detached from the implant 600 by any method known in the art. A person skilled in the art will also appreciate that the implant 600 can be expanded to and kept at any height within its distraction envelope of between about 5 mm and 15 mm.

The self-distracting spinal implants disclosed herein are particularly well suited for minimally invasive surgery. That is, the self-distracting implants disclosed herein have a compressed envelope with a height of about 5 mm and can easily be inserted via a minimally invasive surgery port, without the need of an open surgical procedure. Such procedures, which are generally well known to those skilled in the art, tend to result in less operative trauma for the patient than more invasive procedures. Minimally invasive procedures also tend to be less expensive, reduce hospitalization time, cause less pain and scarring, speed recovery, and reduce the incidence of post-surgical complications, such as adhesions.

In addition to the various features discussed above, the self-distracting spinal implants described herein can be adapted so as to allow for spinal fusion and/or spinal fixation. Any of the implant designs disclosed herein can include or be formed of a fusion-promoting bioactive material so that the implant actively participates in spinal fusion. In an exemplary embodiment, the implant is made from a bioactive material. In another embodiment, a bioactive material can be formed as a coating on a non-bioactive material from which the implant is formed. In still a further embodiment, the implant can be filled with a bioactive material so that bony ingrowth through the implant and between the vertebra is allowed and encouraged. For example, the implant can be formed of a metal or CFRP and be coated or filled with a fusion-promoting bioactive material. Exemplary fusion promoting bioactive materials can include allograft bone, tricalcium phosphates (TCP), hydroxyapatite, Biocryl Rapide™ (tricalcium phosphate loaded poly-L-lactic acid/Poly-glycolic acid), bioglass, plasma sprayed titanium, hydroxyapatite-coated titanium, surface textured titanium, and polymer composites.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for distracting two adjacent vertebrae, comprising:
   accessing an intervertebral disc space between two adjacent vertebrae without distracting the intervertebral disc space;
   surgically delivering a selectively expandable spinal fusion implant into the intervertebral disc space between the two adjacent vertebrae, the implant including a superior endplate, an inferior endplate, a fixed platen member coupled to a first one of the endplates, and a movable platen member coupled to a second one of the endplates; and
   delivering a flowable material into the spinal implant such that the movable platen member slides relative to the fixed platen member and increases a separation between the two adjacent vertebrae until the two adjacent vertebrae are at a desired separation.

2. The method of claim 1, wherein the surgically delivering step is conducted in a minimally invasive surgical procedure.

3. The method of claim 2, wherein the spinal fusion implant is delivered through one of an access port and a cannula.

4. The method of claim 1, wherein the surgically delivering step is conducted while the implant is at a compressed height of about 5 mm.

5. The method of claim 1, further comprising making angular adjustments to at least one of the superior and inferior endplates with respect to a plane extending horizontally therethrough.

6. The method of claim 1, wherein the flowable material comprises a curable material.

7. The method of claim 6, further comprising applying light energy to harden the flowable material in the spinal implant.

8. The method of claim 6, further comprising applying a chemical to cure the flowable material in the spinal implant and maintain the vertebrae at the desired separation.

9. The method of claim 1, wherein the flowable material comprises polymethyl methacrylate (PMMA) bone cement.

10. The method of claim 1, further comprising adjusting an amount of flowable material delivered to the spinal fusion implant.

11. The method of claim 1, wherein the spinal fusion implant is surgically delivered in a compressed position with the superior endplate being parallel to the inferior endplate.

12. The method of claim 1, wherein at least a portion of the movable platen member is disposed in a bore formed in the fixed platen member.

13. The method of claim 12, further comprising an expandable member disposed within the bore of the fixed platen member that receives the flowable material which causes the movable platen member to slide relative to the fixed platen member.

14. A method for distracting adjacent vertebrae, comprising:
   inserting a cage between adjacent vertebrae, the cage including a superior endplate, an inferior endplate, a mid-portion, and first and second articulating joints;
   delivering a fluid to the mid-portion such that the height of the cage increases and distracts the adjacent vertebrae;
   independently adjusting the first articulating joint relative to the mid-portion of the cage, thereby changing an angle of the superior endplate relative to a plane extending horizontally through the mid-portion of the cage; and
   independently adjusting the second articulating joint relative to the mid-portion of the cage, thereby changing an angle of the inferior endplate relative to the plane extending horizontally through the mid-portion of the cage.

15. The method of claim 14, wherein the inserting step is conducted in a minimally invasive surgical procedure.

16. The method of claim 14, wherein the inserting step is conducted while the cage is at a compressed height of about 5 mm.

17. The method of claim 16, wherein the mid-portion of the cage is expanded until the cage has a maximum height of about 15 mm.

18. The method of claim 14, wherein expanding the mid-portion of the cage includes delivering a curable material to an interior of the cage.

19. The method of claim 14, wherein the angle of the inferior endplate and the angle of the superior endplate are adjusted after the mid-portion of the cage is expanded.

20. The method of claim 14, wherein the first and second articulating joints comprise ball joints.

* * * * *